(12) United States Patent
Clarke

(10) Patent No.: US 7,872,051 B2
(45) Date of Patent: Jan. 18, 2011

(54) ANTIVIRAL COMPOSITION COMPRISING P-MENTHANE-3,8-DIOL

(76) Inventor: Paul Douglas Clarke, Friday Island, 2 Kingswood Creek, Buckinghamshire, Wraysbury (GB) TW19 5EN (*) Notice: Subject to any disclaimer, the term of this patent is extended or adjusted under 35 U.S.C. 154(b) by 753 days.

(21) Appl. No.: 10/598,800

(22) PCT Filed: Mar. 2, 2005

(86) PCT No.: PCT/GB2005/000803
§ 371 (c)(1),
(2), (4) Date: Oct. 18, 2006

(87) PCT Pub. No.: WO2005/087209
PCT Pub. Date: Sep. 22, 2005

(65) Prior Publication Data
US 2007/0178048 A1 Aug. 2, 2007

(30) Foreign Application Priority Data

| Mar. 12, 2004 | (GB) | ................................. 0405636.2 |
| Jun. 16, 2004 | (GB) | ................................. 0413518.2 |
| Jun. 25, 2004 | (GB) | ................................. 0414327.7 |

(51) Int. Cl.
*A01N 31/00* (2006.01)
*A61K 31/045* (2006.01)
(52) U.S. Cl. .................................................. 514/724
(58) Field of Classification Search .................. 514/724
See application file for complete search history.

(56) References Cited

U.S. PATENT DOCUMENTS

| 4,856,509 A | * | 8/1989 | Lemelson ............... 128/206.19 |
| 5,017,377 A | | 5/1991 | Sikinami et al. |
| 5,298,250 A | | 3/1994 | Lett et al. |
| 5,698,209 A | | 12/1997 | Shono et al. |
| 5,959,161 A | | 9/1999 | Kenmochi et al. |
| 7,048,953 B2 | | 5/2006 | Vail, III et al. |
| 2004/0009245 A1 | * | 1/2004 | Vail et al. ..................... 424/742 |

FOREIGN PATENT DOCUMENTS

| EP | 1 204 319 B1 | 9/2003 |
| GB | 1 315 625 | 5/1973 |
| GB | 2 282 534 A | 4/1995 |
| JP | 2002000636 | 1/2002 |
| WO | WO 01/05226 | * 1/2001 |
| WO | WO 01/05226 A1 | 1/2001 |

OTHER PUBLICATIONS

Aoshima, Shuji, et al., "Adhesive eye masks containing hydrated gel compositions," Database CA (Online), Chemical Abstracts Service (Jan. 8, 2002), Columbus, Ohio, XP002331699, pp. 1-3.
Barasa, Stephen S., "Repellent Activities of Stereoisomers of p-Methane-3,8-diols Against *Anopheles gambiae* (Diptera: Culicidae)," Journal of Medical Entomology, vol. 39, No. 5 (2002), Entomological Society of America, pp. 736-741.
Muanza, D.N., "Antibacterial and Antifungal Activities of Nine Medicinal Plants from Zaire," Int. J. Pharmacog., vol. 32, No. 4 (1994), Swets & Zeitlinger, pp. 337-345.
Nishimura, Hiroyuki, et al., "Microbial Transformation of Monoterpenes: Flavor and Biological Activity," Chapter 16: Biotechnology For Improved Foods and Flavors (1996), American Chemical Society, pp. 173-187.
Schnitzler, P., et al., "Antiviral activity of Australian tea tree oil and eucalyptus oil against herpes simplex virus in cell culture," Pharmazie, vol. 56, No. 4 (2001), pp. 343-347.
Shahi, Sushil K., et al., "Research Communications: Broad spectrum antimycotic drug for the control of fungal infection in human beings," Current Science, vol. 76, No. 6 (Mar. 25, 1999), pp. 836-839.
Vichkanova, S.A., et al., "Antiviral Activity Displayed by The Essential Oil of E. Viminals And of Some Other Frost-Hardy Eucalypti," Farmakologiya I Toksikologiya, vol. 36, No. 3 (1973), Moscow, pp. 339-341, abstract—p. 341.
Zimmerman, Howard E., et al., "Stereoisomerism of Isopulegol Hydrates and Some Analogous 1,3-Diols," Contribution No. 1116, Sterling Chemistry Laboratory, Yale University (May 20, 1953), New Haven, Connecticut, pp. 2367-2370.
Pest Management Regulatory Agency, Proposed Regulatory Decision Document (PRDD2002-02), "p-Menthane-3,8-diol: OFF! Botanicals Lotion Insect Repellent 1" (Sep. 18, 2002), Ottawa, Ontario, Canada, 22 pgs.
Foreign communication from a counterpart application—International Search Report, PCT/GB2005/000803, Jun. 28, 2005, 3 pages.
Foreign communication from a counterpart application—International Preliminary Report on Patentability, PCT/GB2005/000803, Sep. 13, 2006, 7 pages.

* cited by examiner

*Primary Examiner*—Johann R Richter
*Assistant Examiner*—Kristie L Brooks
(74) *Attorney, Agent, or Firm*—Conley Rose, P.C.; Rodney B. Carroll

(57) ABSTRACT

The use of p-menthane-3,8-diol (PMD) in the manufacture of a medicament for use as an antiviral agent. The use of PMD in the manufacture of a medicament to destroy or inactivate viruses. The use of PMD, in vitro, as an antiviral or virucidal agent. The use of PMD in the manufacture of a medicament for the treatment of diseases caused by viruses having a lipid envelope. A face mask comprising at least one protective layer impregnated or sprayed with PMD.

15 Claims, 4 Drawing Sheets

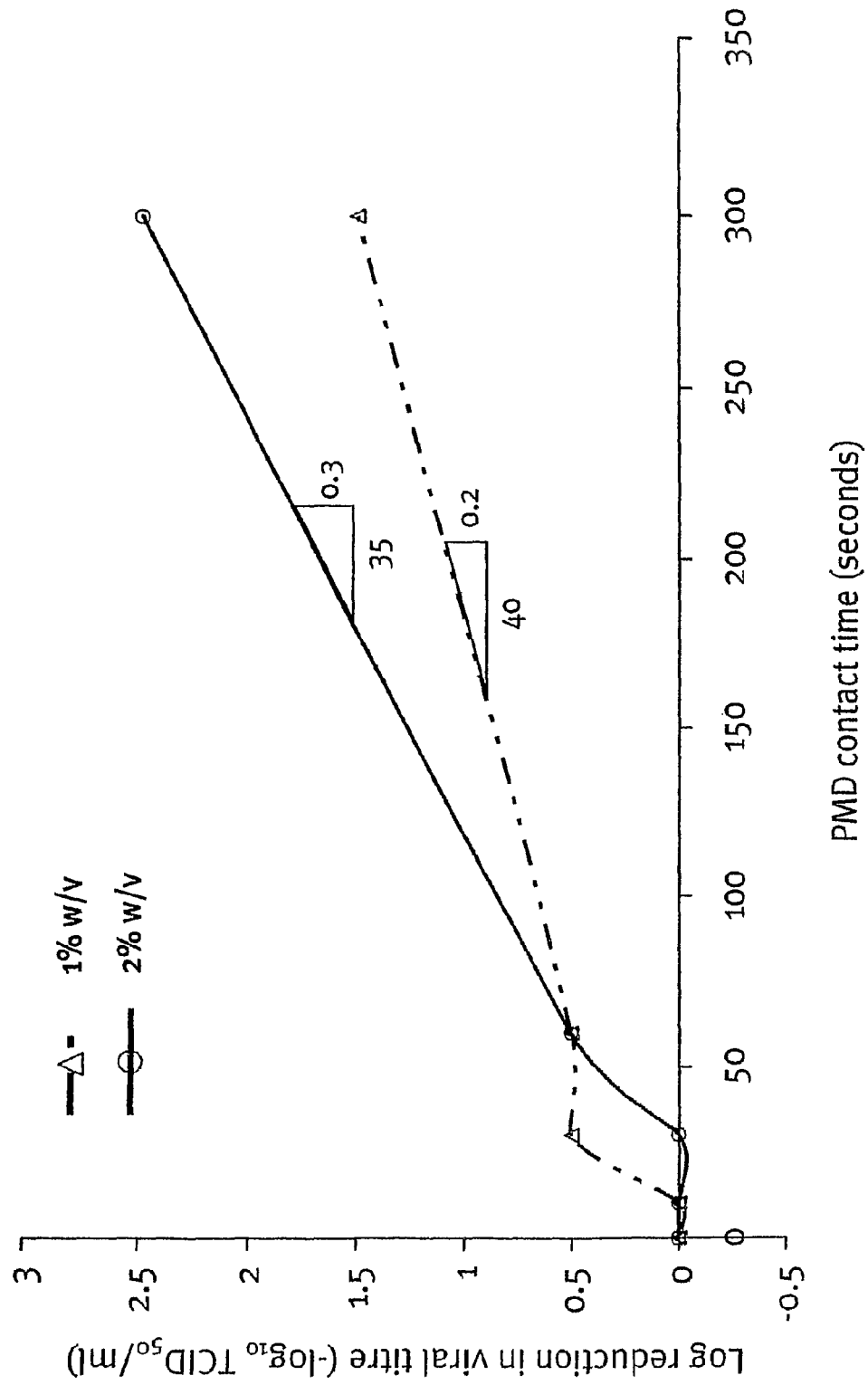
Figure 2 Illustrating the log reduction in viral titre of HSV-1 virus after treatment with different concentrations of PMD for different contact times Figure 3 Illustrating the log reduction in viral titre of Urbani SARS virus after treatment with different concentrations of PMD for different contact times

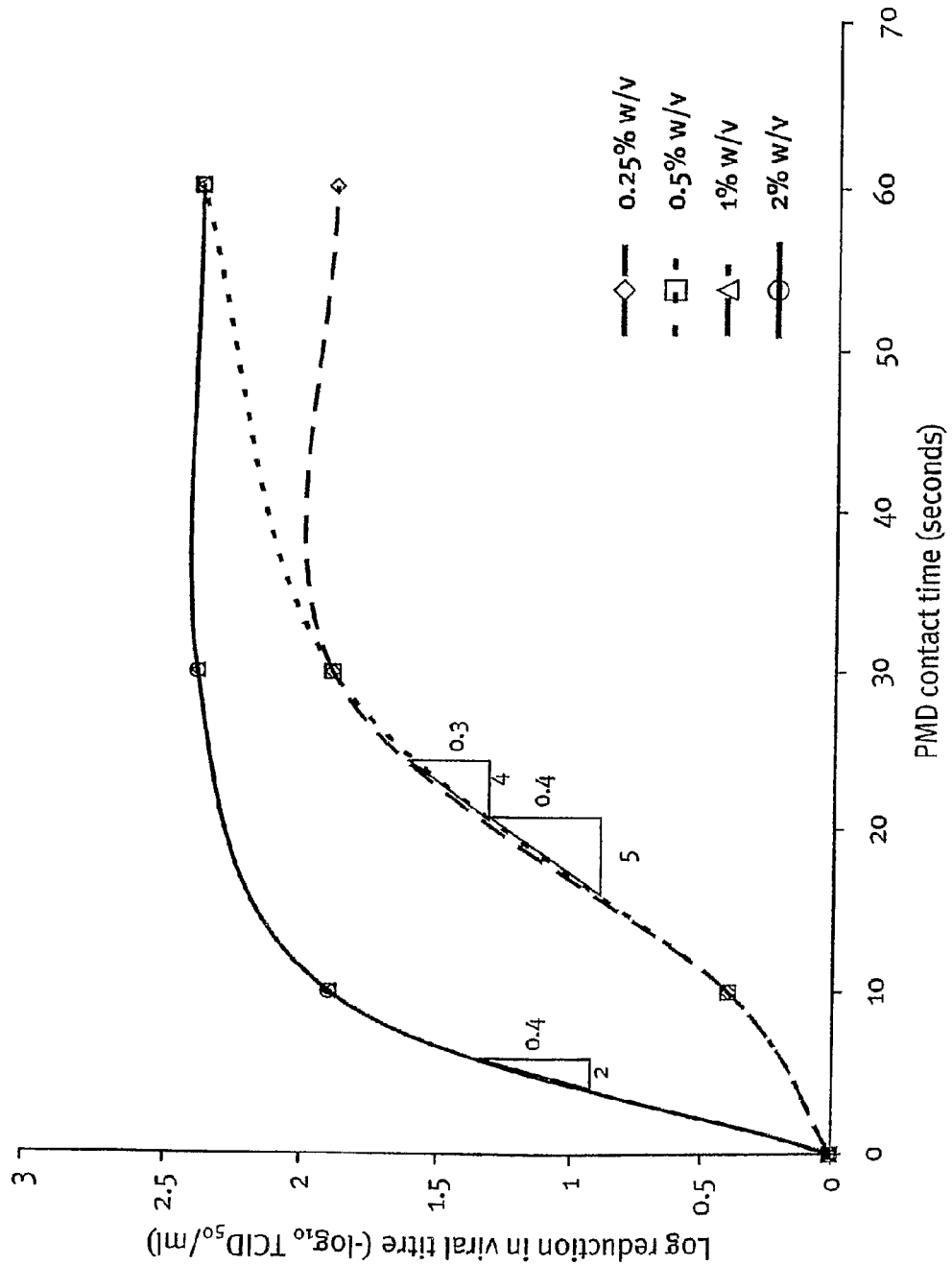
Figure 4 - Illustrating the log reduction in viral titre of A/Sydney/5/97 after treatment with different concentrations of PMD for different contact times

ANTIVIRAL COMPOSITION COMPRISING P-MENTHANE-3,8-DIOL

CROSS-REFERENCE TO RELATED APPLICATIONS

This application is a filing under 35 U.S.C. 371 of International Application No. PCT/GB2005/000803 filed Mar. 2, 2005, entitled "Antiviral Composition Comprising P-Menthane-3,8-Diol," claiming priority of Great Britain Patent Application Nos. GB0405636.2 filed Mar. 12, 2004, GB0413518.2 filed Jun. 16, 2004 and GB0414327.7 filed Jun. 25, 2004, which applications are incorporated by reference herein in their entirety.

FIELD OF THE INVENTION

The present invention relates to an antiviral composition.

BACKGROUND OF THE INVENTION

It is known that a number of natural products have insect repellent properties. Citronella oil, which is obtained from certain grasses, is one example of such a natural product, and oil from the Neem tree is another. We have previously investigated Eucalyptus citriodora and found that it possesses insect repellent properties. The repellent properties are found in a fraction rich in p-menthane-3,8-diol (PMD). This is described in our GB-A-2282534.

In GB-A-1315625, there is described the use of certain p-menthane diols, but not p-menthane-3,8-diol (PMD), to provide a physiological cooling effect.

EP-B-1204319 describes the use of PMD as an antiseptic and antifungal agent.

SUMMARY OF THE INVENTION

We have now found, surprisingly, that PMD also possesses antiviral properties.

According to one aspect of the invention, we provide the use of PMD in the manufacture of a medicament for use as an antiviral agent.

According to another aspect of the invention, we provide the use of PMD in the manufacture of a medicament to destroy or inactivate viruses.

According to another aspect of the invention, we provide the use of PMD, in vitro, as an antiviral or virucidal agent.

According to a further aspect of the invention, we provide the use of PMD in the manufacture of a medicament for the treatment of diseases caused by viruses having a lipid envelope.

According to a further aspect of the invention, we provide a face mask comprising at least one protective layer impregnated or sprayed with PMD.

DETAILED DESCRIPTION OF THE INVENTION

It is to be understood that the term "virucidal", as used in this specification, means "having the capacity to destroy or inactivate viruses". It is also to be understood that the term "antiviral", as used in this specification, means "having the capacity to inhibit or stop the growth and reproduction of viruses", or "having the capacity to destroy or inactivate viruses". The use of PMD in the present invention may be virucidal or antiviral.

The PMD for use in the present invention may be derived from a natural source or may be synthetic, or a mixture of the two. A preferred source of natural PMD is the lemon eucalyptus plant Eucalyptus citriodora. Synthetic PMD may be obtained by any route, for example, such as described by Zimmerman and English in J.A.C.S. 75 (1953) pp 2367-2370. PMD is also a precursor obtained during the synthesis of menthol. The precursor is usually in the form of a specific isomer of PMD.

The PMD for use in the present invention may be a substantially pure form of the compound, or a crude extract, for example from a natural source. An example of a crude extract is a PMD-rich extract derived from lemon eucalyptus by acid modification of lemon eucalyptus oil. The PMD can be produced by cyclisation of citronellal which is present in high concentration in lemon eucalyptus oil (approximately 75% by weight). We have obtained a PMD-rich extract from the lemon eucalyptus oil which includes both geometric isomers of PMD, usually at about 64% of PMD in the extract by weight. The crude extract also includes citronellol and isopulegols plus certain other minor components.

Thus, in accordance with the present invention, it is contemplated that the PMD used in the present invention may be provided in the form of a PMD-rich extract, which is derived from natural lemon eucalyptus oil. An example of this sort of crude extract is available under the trade mark "Citriodiol". Citriodiol may be used as the source of PMD in the present invention.

A composition for use in accordance with the invention generally comprises PMD and a carrier. PMD is poorly soluble in water, so it is preferred to use an oil as a carrier, or to use a solvent, such as alcohol, for water-based compositions.

It is known that PMD exists in two geometric isomeric forms, namely the cis and trans isomers. Altogether, there are 8 isomers of PMD, as shown in FIG. 1. This invention encompasses any single one isomer and also any combination of one or more isomers.

Our experimental work is based on the 98% pure cis isomer. It will be understood, however, that the claimed activities for PMD are common to all its isomeric forms. Thus, the PMD may be used in the form of a single pure cis or trans isomer, or in the form of a mixture of the isomers, with any appropriate proportion of each isomer. PMD is normally produced in a mixture of cis:trans at about 2:1, and this mixture is perfectly acceptably. However, a 50:50 mixture of the cis and trans isomers may instead be used, as may other mixtures.

In an embodiment, the composition for use in the invention comprises only one of the isomers of PMD, with a carrier therefor.

In another embodiment, the relative amounts of cis:trans PMD isomers in the compositions for use in the present invention are varied as desired. This can be done by mixing previously separated isomers in the appropriate ratio, or by adjusting the ratio in a mixture of naturally derived PMD or PMD from a synthetic source.

In tests we have found that PMD is effective against influenza, as exemplified by the effectiveness of PMD against the influenza virus A/Sydney/5/97. We have also found that PMD is effective against Urbani Severe Acute Respiratory Syndrome (Urbani SARS) and Herpes caused by the Herpes Simplex Virus type-1 (HSV-1). PMD may also be used to treat Herpes Simplex Virus type-2 (HSV-2).

In an embodiment of the present invention, therefore, the PMD is used to treat influenza. In a further embodiment, the PMD is used to treat influenza caused by the virus A/Sydney/5/97. In another embodiment, the PMD is used to treat Urbani SARS. In another embodiment, the PMD is used to treat Herpes caused by Herpes Simplex Virus type-1 (HSV-1).

Influenza viruses, including A/Sydney/5/97 and viruses which fall within the A and B types of influenza, Urbani SARS and Herpes Simplex virus type-1 all possess a lipid envelope. Other examples of viruses having a lipid envelope include coronaviruses (one of which is Urbani SARS), Herpes Simplex Virus type-2 (HSV-2), Human Immunodeficiency Virus (HIV), Hepatitis B, Hepatitis C, West Nile virus, Vesicular stomatitis virus, Sindbis virus and Sendai virus.

The uses of the present invention may be adopted in sanitizing a surface, for example in a hospital room or ward. In such cases PMD is applied to the surface. The PMD is preferably either in solution or present as an emulsion in suitable liquid carriers. Most desirably, the PMD is formulated for spray application. For example, the PMD or Citriodiol can be dissolved in a suitable solvent or solvent mixture. For example, in one embodiment, the PMD may be provided in the form of a nasal spray; in another embodiment, the PMD may be provided in the form of a spray for telephones.

In one mode of application, the spray is an electrostatic spray. For electrostatic spraying, the solvent or solvent system will need to be appropriate for electrostatic spraying, as will be clear to those skilled in the art. It is preferable to use a mixture of conductive and nonconductive solvents to achieve a sprayable solution with the appropriate electrical resistivity for the spray nozzle in question, but suitable single solvents can be used. Charged particles of the composition including PMD are projected as a fine mist and because all the particles carry a similar, for example positive, charge, they repel each other, but are attracted to an oppositely charged surface. By this means of spraying, a very good coverage of the composition on the surface may be obtained. Devices for electrostatically spraying the composition for use in the invention will be known to the person skilled in the art.

To increase the likelihood of the charged particles covering the skin surface, the electrostatic spray nozzles may desirably be arranged to spray into the interior of a cabinet or container as the hand is introduced therein.

An electrostatic spray or a simple atomised spray may also be used, for example, for dispensing a composition including PMD onto a hand (or other part) of a person. The actuation of the dispenser may be by means of an infra-red sensor, for example, so that the person need not contact a surface, and thereby risk the transfer of viruses to or from their hand. Spray application to a hand may be used, with advantage, where a substantially uniform coverage of antiviral agent is particularly important e.g. to a surgeon during "scrubbing up" before surgery.

The liquids for applying to a surface, by spraying or otherwise, in accordance with the invention may contain, apart from the solvent(s) and/or other liquid carrier(s), other components as necessary or desirable for the intended purpose. Thus, second or further antiviral agents may be included, as may surfactants, fragrances etc. In general, the compositions may be identical to known compositions for the purpose except that they contain PMD in addition to, or in whole or part substitution for one or more of, the other ingredients.

The amount of PMD required to have an antiviral effect may vary widely between different viruses and also on the time in contact with the virus. Thus, we have shown that at 10 seconds' contact time, at least a 1% w/v PMD concentration is desirable to have a significant antiviral action against A/Sydney/5/97 Influenza virus, while for Urbani SARS even 0.25% for 10 seconds' exposure is effective. In contrast, at least 1% w/v PMD is desirable for the prolonged contact time of 5 minutes to have a significant effect on the Herpes virus HSV-1 in our laboratory tests. Thus routine experimentation is required to decide the optimum concentration of PMD and the optimum time for contact for any specific virus.

PMD may also be included as an antiviral agent in household detergents, cleansers and creams, for example, washing powders or conditioners and hand gels. Again, the PMD may be included in what are otherwise standard or known compositions for the purpose concerned. The PMD may be an extra ingredient or in partial or complete replacement of a standard ingredient. The compositions may already contain an antiviral agent and the PMD is added to give an extra antiviral effect.

Furthermore, PMD may be impregnated into household objects which may be prone to virus infestation and so risk infecting inhabitants, e.g. dishcloths, plastic soap dishes, surfaces used for the preparation of food.

For these purposes, the PMD may be included during manufacture of the object, e.g. in mixtures for plastics mouldings or the like, or it may be applied to the object after manufacture, e.g. by soaking dishcloths in PMD. The presence of the PMD at the surface of the object will provide the desired antiviral effect. This is particularly useful for work surfaces, although such surfaces can also be regularly treated with PMD, by spraying or otherwise.

Therefore, according to another aspect of the invention there is provided a method of destroying or inactivating viruses on a surface comprising applying PMD thereto, wherein the surface is not a surface of a human or animal body. The surface may be on the wall, floor, ceiling or other structural part of a room or building; or an equipment or apparatus; or may be a work surface. The PMD or PMD composition may be applied by spraying or electrostatic deposition. The surface may be a surface of a glove.

According to another aspect of the invention there is provided the use of PMD in a household product such as a detergent, cleanser or cream, to provide antiviral or virucidal properties.

According to another aspect of the invention there is provided the use of PMD as an antiviral or virucidal agent in a sterile surgical scrub solution.

PMD may be sprayed onto face mask material or impregnated into such material during manufacturing to prevent both ingress and egress of viable viral particles, towards or away from the individual. Thus the individual may be protected from viruses transmitted from another infected person or may use the mask to prevent his own infection being passed on to others. This would be of particular use against those viruses spread by droplet spray or aerosol. The PMD spray may be applied to either the outside or inside of the mask, or both. In masks made with replaceable filters, the filters may be similarly sprayed or impregnated during manufacture to allow replenishment in the most cost effective way. This would particularly apply to masks now being designed to look attractive and be reused repeatedly with replaceable filters. It may also be possible to impregnate the filters within air conditioning systems whether in hotels or in aeroplanes or other vehicles where public use is heavy.

The face mask in accordance with the invention may be any mask conventionally used to protect a user from harmful material in the surrounding atmosphere. Typically the face mask includes at least one filter layer, and a means to secure the mask to the face of a user. In an embodiment, the securing means may include a band adapted to extend around the back or the head of the user, or adapted to be secured to the ears of the user; the band may be an elastic material, so that the mask can easily be fitted to a wide variety of different individuals. The mask may have more than one filter layer.

In many circumstances it is desirable to include a flexible nose strip in the mask. The purpose of the strip is to shape the mask to follow the contours of the nose, to decrease the likelihood of air bypassing the mask material. Masks incorporating such a strip are more effective in preventing the ingress or egress of droplets, by ensuring that the wearer breathes through the mask material. The strip may be formed of aluminium, and is typically around 50 mm in length.

Although the primary use of the PMD impregnated mask is to provide protection against viruses, it will be noted that PMD is also an antibacterial and antifungal agent, (see EP-B-1204319), therefore the mask can also be effective to prevent ingress or egress of bacterial or fungal material.

The invention also provides a method of making a face mask effective to prevent the ingress or egress of viruses, comprising spraying the mask or impregnating the mask with PMD or a PMD containing composition.

Additionally, PMD may be incorporated into pre-wetted wipes, for use, for example, in cleaning masks, lavatory seats, door handles or elevator buttons.

A composition including PMD can also be used in medicine. Thus, the invention includes a pharmaceutical formulation containing PMD and a pharmaceutically acceptable carrier, for antiviral or virucidal use. For example, the pharmaceutical composition can be applied to broken skin, or to internal mucous membranes. It may be an ingredient in throat lozenges or pastilles or other products for ingestion. In medical uses the PMD may be formulated with the carrier as a cream, or, as mentioned above, as a throat lozenge or pastille. A composition including PMD may be applied to the accessible inner surfaces of the nose in order to control or eliminate viruses which may cause regular systemic effects. For these purposes, PMD may be formulated as a nasal spray. Another specific medical use is in wound irrigation during surgery, e.g. surgery conducted on the peritoneal cavity.

In one advantageous formulation, the PMD is formulated with petroleum jelly as an ointment, preferably for topical administration.

As will be evident to those skilled in the art, there are a very large number of medical uses of PMD as an antiviral or virucidal agent. In general, new formulations for these purposes are not required: it is adequate and satisfactory to take a known or standard composition and include the PMD therein. Alternatively, one or more ingredients may be replaced by the PMD as appropriate. Those skilled in the art will well know the make-up of the various compositions and no further particular description thereof is given here.

PMD is the active ingredient in the insect repellent sold under the trade name "Mosiguard"™. Extensive tests have already been conducted to show regulatory authorities that Citriodiol™, which contains about 64% PMD is not toxic. Mosiguard insect repellent has been marketed for about ten years and there has been no report of any significant toxicity thereof. Potentially, therefore, the medical uses of PMD may be topical or systemic. Systemic administration may be by way of an oral dosage form or by a parenteral route, such as by intra-venous, intra-muscullar or sub-cutaneous injection.

In general, PMD is used in accordance with the invention in a wide variety of vehicles, depending on the particular use intended. The vehicles may, for example, include solids, liquids, emulsions, foams and gels.

Typical vehicles include aqueous or alcoholic solutions, oils, fats, fatty acid esters, long chain alcohols and silicone oils, finely divided solids such as starch or talc, cellulosic materials and aerosol propellants. Topical compositions include perfumes, powders and other toiletries, lotions, liniments, oils and ointments, for example. Toiletries generally include after shave lotions, shaving soaps, lipstick, creams, foams, toilet water, deodorants, antiperspirants, solid colognes, toilet soaps, bath oils and salts, shampoos, face and hand creams, cleansing tissues, mouthwashes, eye drops, for example. Medicaments and allied compositions include, for example, ointments, lotions, decongestants and throat lozenges. The amount of PMD present in the compositions will be selected to give the desired effect but we believe that generally up to 5.0 wt %, preferably from 0.25 wt % to 5.0 wt % will be satisfactory. Greater amounts can be used. A particularly preferred concentration is from 1.0 to 3.0 wt %, especially about 2 wt %.

A PMD-rich extract may be obtained from PMD-containing material, such as the leaves of a eucalyptus plant. A preferred source of PMD rich extract is obtained by stirring eucalyptus citriodora oil derived from the plant with dilute sulphuric acid (usually 5% sulphuric acid), as previously explained in our GB-A-2282534.

In order that the invention may be fully understood, the following examples are given by way of illustration only.

BRIEF DESCRIPTION OF THE DRAWINGS

Reference is now made to the accompanying drawings, in which:

FIG. 2 illustrates the log reduction in viral titre of HSV-1 virus after treatment with different concentrations of PMD for different contact times.

FIG. 3 illustrates the log reduction in viral titre of Urbani SARS virus after treatment with different concentrations of PMD for different contact times.

FIG. 4 illustrates the log reduction in viral titre of A/Sydney/5/97 virus after treatment with different concentrations of PMD for different contact times.

TRIALS

Figure 1:
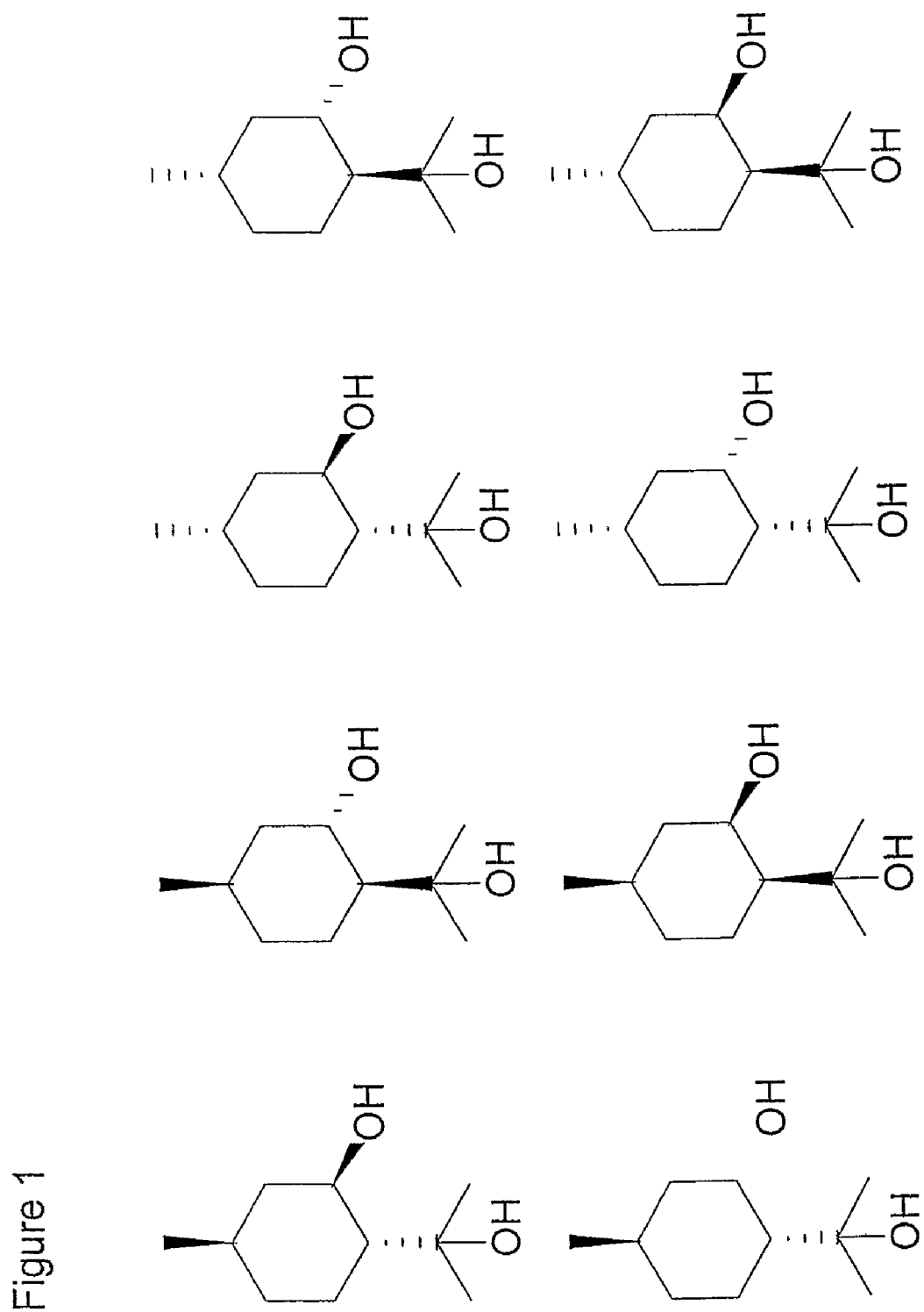
FIG. 1 illustrates the eight isomers of PMD.

Three trials were carried out: the first on the influenza virus A/Syney/5/97 (Trial 1); the second on three viruses, namely A/Sydney/5/97, Urbani SARS and HSV-1 (Trial 2); and the third on the virucidal activity of PMD against an influenza A virus and Urbani SARS virus when applied to a face mask.

Trial 1

Procedure 1

Procedure for the Acute Toxicity Assay of PMD

The toxicity of PMD at the following concentrations in cell maintenance media was determined on a cell line with MDCK cells:

2.5 mg/ml (0.25% w/v)

5 mg/ml (0.5% w/v)

20 mg/ml (2% w/v)

A cell only control was also implemented by following the same procedure (steps 2-6), but substituting PMD with cell maintenance media.

Toxicity was determined by toxicity-induced CPE (cytopathic effect) observations, which was visually scored using microscopy techniques. Toxicity-induced CPE is characterised by burst or rounded cells, which have become dissociated from their neighbouring cells, or the presence of cellular debris. Toxicity-induced CPE was scored as positive (toxicity observed) or negative (no toxicity observed).

(1) 200 μl of each PMD dilution was added to 200 μl of cells (at 2×10⁶ cells/ml) and the reaction incubated for 5 minutes at room temperature.
(2) The reaction was terminated by adding 3.6 ml of cell maintenance media appropriate to the cell line.
  Note: termination of the reaction is due to the addition of cell maintenance media, which dilutes the reaction 10-fold.
(3) 100 μl of the terminated reaction was added to the relevant wells on 48-well plates and incubated for 24 hours at 37° C., 5% $CO_2$.
  Note: the remaining terminated reaction was measured for levels of pH.
(4) The cells in the 48-well plate were trypsinised and a viable cell count was performed using the Trypan blue dye. The percentage of viable cells was used to determine the toxic concentration of PMD in comparison to the cells only control.

Procedure 2

Procedure for the Virucidal Assay of PMD

The virucidal assay was carried out using four different concentrations of PMD, which do not exhibit toxicity (based on the data obtained from the procedure described in 1).
The four concentrations are as follows.
2% w/v (20 mg/ml)
0.5% w/v (5 mg/ml)
0.25% w/v (2.5 mg/ml)
0.1% w/v (1 mg/ml)
The stock virus was used at a titre greater than $10^4$ $TCID_{50}$/ml.

The appropriate positive anti-viral control compound was citric acid.

The presence and absence of viral infection was determined by infection-induced CPE observation, which was visually scored using microscopy techniques. Infection-induced CPE differs between viruses, but is normally characterised by ballooning or rounded cells that remain attached to their neighbouring cells. It was scored as positive (infection apparent) or negative (infection not apparent).
(1) MDCK cell lines were cultivated according to the current Retroscreen Virology Ltd. SOP onto 96-well plates.
(2) 40 μl of A/Sydney/5/97 virus was added to 360 μl of each PMD dilution and citric acid.
  Note: The virus was diluted 10-fold in this step.
(3) The reactions were incubated at room temperature for the following contact times:
  10 seconds
  30 seconds
  1 minutes
  5 minutes
(4) At each contact time point, the reaction was terminated by adding 3.6 ml of infection media appropriate to the cell line.
  Note: termination of the reaction is due to the addition of infection media, which dilutes the reaction 10-fold.
(5) 100 μl of the terminated reaction was added to the first column of 96-well plates (prepared in point 1) and titrated across the plate following a ¹⁄₁₀ dilution series.
  Note: the remaining terminated reaction was measured for levels of pH.
(6) The cells were incubated for 3-5 days at 37° C., 5% $CO_2$.
(7) CPE was scored daily on the plates to determine the presence or absence of infection. The reduction in viral titre (as a result of anti-viral activity of PMD and the positive control compound, citric acid) was determined.

The results showed that using an influenza virus A/Sydney/5/97 on MDCK cells, there was no viral replication as evidenced by cell survival with 2% w/v PMD in the culture medium. At lower concentrations (0.5%, 0.25% and 0.1%) cells were killed indicating no virucidal effect at these levels.

Trial 2

Procedure 1

Procedure for the Acute Toxicity Assay of PMD
The viruses used in the study were:
HSV-1 (Herpes Simplex Virus type 1)
Urbani SARS
A/Sydney/5/97 (human influenza virus H3N2)
PMD was tested at the following concentrations:
2% w/v (20 mg/ml)
1% w/v (10 mg/ml)
0.5% w/v (5 mg/ml)
0.25% w/v (2.5 mg/ml)
The cell line appropriate for each virus is shown in Table 1.

TABLE 1

Viruses and their appropriate cell lines

| Virus | Cell Line |
|---|---|
| HSV-1 | Vero |
| Urbani SARS | C1008 |
| A/Sydney/5/97 | MDCK |

Each PMD concentration was made up in 100% isopropyl and then sufficient cell infection media added such that the final concentration of isopropyl was always 10%.

The different concentrations were made up by taking into account the initial dilution of the compound that occurs in the toxicity assay (step 1) and virucidal assay (step 4). The dilution factors for both assays are 2 and 1.1, respectively. Table 2 details the initial PMD concentrations made up for both assays.

TABLE 2 initial PMD concentrations for the toxicity and virucidal assays and the dilution factor the compound undergoes for each assay

| Final PMD concentration (% w/v) | Initial PMD concentration (% w/v) | |
|---|---|---|
| | Toxicity assay | Virucidal assay |
| 0.25 | 0.5 | 0.28 |
| 0.5 | 1 | 0.56 |
| 1 | 2 | 1.11 |
| 2 | 4 | 2.22 |

Each of the four PMD concentrations was tested for toxicity on each of the three cell lines.

A "cell only" control was also implemented by following the same procedure but substituting PMD (step 1) with infection media.

The procedure for the toxicity assay was as follows:
1) Cells (200 μl), at 2×10⁶ cells/ml, were added to PMD (200 μl) and the reaction incubated for 5 minutes at room temperature.
2) The reaction was terminated by the addition of infection media (3.6 ml) appropriate to the cell line.
3) The terminated reaction (1 ml) was added, in triplicate, to the relevant wells of a 24-well plate.

4) The cells were incubated for 24 hours at 37° C., 5% $CO_2$.
5) After the incubation period, the cells were trypsinised, the appropriate triplicate wells pooled together and a viable cell count performed using Trypan blue dye.
6) The toxicity of PMD was determined by calculating the percentage cell survival of the test cells in comparison to the control cells.

The results of the toxicity assay for the different concentrations of PMD are shown in Table 3.

TABLE 3

Percentage cell survival of three different cell lines treated with either 10% isopropyl or three different concentrations of PMD

| Cell Line | 10% Isopropyl | *Percentage cell survival (%) PMD concentrations (% w/v) | | |
|---|---|---|---|---|
| | | 0.25 | 0.5 | 2 |
| C1008 | 100 | 80 | 60 | 100 |
| MDCK | 40 | 40 | 100 | 85 |
| Vero | 100 | 65 | 65 | 100 |

*values are rounded to the nearest 5

The toxicity of 10% isopropyl was tested to eliminate it as a possible toxic component of the final preparation of PMD.

The 1% w/v PMD concentration was not tested in this assay.

Procedure 2

Procedure for the Virucidal Assay of PMD

Two types of controls were used in the virucidal assay:
A positive anti-viral control compound (detailed in Table 4)
A diluent control—10% isopropyl—was used as the solvent in the preparation of each PMD concentration. Therefore, it had to be made certain that this reagent did not possess any virucidal activity against any of the viruses.

TABLE 4

Viruses and their appropriate positive control compounds for the virucidal assay

| Virus | Positive control compound |
|---|---|
| HSV-1 | 100% DMSO |
| Urbani SARS | 1% Triton-X |
| A/Sydney/5/97 | Citrate buffer, pH 3.5 |

The non-toxic PMD concentrations were tested for their virucidal activity against each of the three viruses.

Each virus stock was used at a titre of at least $10^3$ $TCID_{50}$/ml.

The procedure for virucidal assay was as follows:
Preparation of 96-Well Plates
1) Each cell line ($3\times10^5$ cells/ml) was seeded onto 96-well plates and left to incubate for 24 hours or until they were 80% confluent.
2) The maintenance media on the plates was removed and the cell monolayers washed with PBS.
3) Infection media (100 µl) appropriate to each cell line was added to the plates.
Preparation of the Virucidal Reaction
4) Virus (40 µl) was added to each PMD concentration (360 µl) as detailed in procedure 1.
5) The test reactions were incubated at room temperature for the following contact times:

10 seconds
30 seconds
60 seconds (1 minute)
300 (5 minutes)
6) After each contact time, the reactions were terminated by the addition of infection media (3.6 ml) appropriate to the cell line.
Titration and Incubation
7) The infection media in the first column of wells of the 96-well plates (prepared in step 1-3) was removed and replaced with the terminated reactions (110 µl), which were plated in duplicate.
8) The terminated reactions were then titrated across the plate following a 10-fold dilution series.
9) The cells were incubated for 5 days at 37° C., 5% CO2.
10) CPE was scored daily from day 3 post-infection, until day 5 post-infection. In addition, a haemagglutination assay was carried out on day 5 post-infection for the A/Sydney/5/97 virucidal assay only.
11) Any reduction in viral titre for each PMD concentration at each time point, and for the control compounds, was calculated by comparison with the "virus only" control.
12) The assay was also carried out for the antiviral control substances and 10% isopropyl against each virus for the 5 minute contact time.

Tables 5, 6 and 7 show the results of the virucidal assays for HSV-1, Urbani SARS virus and A/Sydney/5/97, respectively.

The results indicate the log reductions in viral titre of each virus in the presence of different PMD concentrations, for different contact times.

A reduction of 1 $\log_{10}$ $TCID_{50}$/ml or greater, (Oxford, J. S. et al, 1994) is considered significant for this assay, and is equivalent to a 90% reduction in viral titre.

TABLE 5 log reductions in viral titre of HSV-1 after treatment with PMD at different concentrations for different contact times

| PMD concentration | Log reduction in viral titre ($-\log_{10}$ $TCID_{50}$/ml) PMD contact time (seconds) | | | |
|---|---|---|---|---|
| (% w/v) | 10 | 30 | ‡60 | †300 |
| 0.25 | 0 | 0 | 0 | 0.5 |
| 0.5 | 0 | 0 | 0 | 0 |
| 1 | 0 | 0.5 | 0.5 | 1.5 |
| 2 | 0 | 0 | 0.5 | 2.5 |

‡1 minute
†5 minutes

TABLE 6 log reductions in viral titre of Urbani SARS after treatment with PMD at different concentrations for different contact times

| PMD concentration | Log reduction in viral titre ($-\log_{10}$ $TCID_{50}$/ml) PMD contact time (seconds) | | | |
|---|---|---|---|---|
| (% w/v) | 10 | 30 | ‡60 | †300 |
| 0.25 | 1 | 2 | 1.5 | 2 |
| 0.5 | 1.5 | 2.5 | 2.5 | 2.5 |
| 1 | 2 | 1.5 | 2 | 1.5 |
| 2 | 1.5 | 1 | 1.5 | 1.5 |

‡1 minute
†5 minutes

TABLE 7 log reductions in viral titre of A/Sydney/5/97 after treatment with
PMD at different concentrations for different contact times

| PMD concentration | Log reduction in viral titre ($-\log_{10}$ TCID$_{50}$/ml) PMD contact time (seconds) | | | |
|---|---|---|---|---|
| (% w/v) | 10 | 30 | ‡60 | †300 |
| 0.25 | 0.4 | 1.9 | 1.9 | 1.4 |
| 0.5 | 0.4 | 1.9 | 2.4 | 1.9 |
| 1 | 1.9 | 2.4 | 2.4 | 2.4 |
| 2 | 1.9 | 2.4 | 2.4 | 2.4 |

‡1 minute
†5 minutes

The kill rates of different concentrations of PMD are illustrated in Table 8.

The kill rate of PMD against HSV-1 at the 0.25% w/v and 0.5% w/v concentrations is not shown as the results for virucidal assay of this virus indicate that the compound did not exhibit any antiviral activity at these concentrations.

TABLE 8

Kill rate of different concentrations of PMD against Urbani SARS
virus, A/Sydney/5/97 and HSV-1

| PMD concentration | Kill rate ($-\log_{10}$ TCID$_{50}$/ml/min) | | |
|---|---|---|---|
| (% w/v) | HSV-1 | Urbani SARS | A/Sydney/5/97 |
| 0.25 | — | 4.0 | 4.5 |
| 0.5 | — | 6.0 | 4.8 |
| 1 | 0.3 | 6.0 | 12.0 |
| 2 | 0.5 | 6.0 | 12.0 |

The kill rate values were calculated from the gradients of the lines plotted in FIG. 2, FIG. 3 and FIG. 4, which graphically represent the results obtained for the HSV-1, Urbani SARS virus and A/Sydney/5/97 virucidal assays, respectively. The figures illustrate the log reductions in viral titre of the viruses, in the presence of different concentrations of PMD over time.

FIG. 3 and FIG. 4 do not show data points for the 5 minute contact time because the results at this time point plateau and show no further significant change.

The measurements of the line gradients were taken after or about the $1-\log_{10}$ TCID$_{50}$/ml point, as the data before this point are deemed non-significant for the virucidal assay.

Results

HSV-1 Virucidal Assay

The results in Table 5 indicate that the virucidal activity of PMD is time and concentration dependent against HSV-1.

Significant reduction in viral titre was observed for the 1% w/v and 2% w/v concentrations at the 5 minute contact time only. For all other concentrations and contact times, no significant reduction in viral titre was observed.

Although the kill rate of PMD against HSV-1 is not as high as that of the Urbani SARS and A/Sydney/5/97 viruses, it still follows the same trend with the kill rate increasing with increasing PMD concentration. As indicated in Table 8, the kill rate of PMD for HSV-1 has almost doubled from the 1% w/v concentration to the 2% w/v concentration.

The measurement of kill rate for HSV-1 was taken from between the 1 minute and 5 minute time-points. FIG. 2 illustrates a gradual increase in log reduction between the 1 minute and 5 minute time points.

Urbani SARS Virucidal Assay

Table 6 shows that all four concentrations of PMD exhibit significant reductions in viral titre at all contact times. It also shows that the compound exhibits neither a time-dependent nor a concentration-dependent activity against the virus.

The kill rates of PMD against Urbani SARS virus, as illustrated in Table 8, are high. However, neither increasing the concentration of PMD nor the contact time, increased the effectiveness of PMD as a virucide, as each concentration produced similar kill rates. A/Sydney/5/97 Virucidal Assay The results in Table 7 show that PMD significantly reduces A/Sydney/5/97 infection at all concentrations tested, except 0.25% w/v and 0.5% w/v at the 10 second contact time.

The 1% w/v and 2% w/v concentrations reduced the viral titre by 1.9-2.4 $\log_{10}$ TCID$_{50}$/ml at all contact time points, whereas the two lower concentrations achieved this at the 30 second to 5 minute contact times only.

Table 8 gives an indication of kill rate of A/Sydney/5/97 over a minute. The kill rate of PMD at all concentrations is high and almost triples from the 0.5% w/v concentration to the 1% w/v concentration.

Trial 3

Mosi-Guard™ was used as the source of PMD.

The four types of masks tested were:

GR8-1: Tecnol "Fluidshield" PFR95 (N95 Particulate Filter Respirator) manufactured by Kimberley-Clarke Corp.

GR8-2: Japanese mask manufactured by Kyrura Co.

GR8-3: Chinese mask, gauze type

GR8-4: Chinese mask, gauze type

Masks GR8-3 and GR8-4 were purchased in local stores in Beijing, China.

The controls utilised in this trial were:

Cell only control—cells (in the absence of virus) incubated with infection media (A/Sydney/5/97 virucidal assay) or cell maintenance media (Urbani SARS virucidal assay) only. This is a negative control for tCPE (toxic cytopathic effect) and vCPE (viral cytopathic effect). It is also an indicator of cell quality.

Cytotoxicity control—cells (in the absence of virus) incubated with infection media (vero cells that are used in the A/Sydney/5/97 virucidal assay) or cell maintenance media (C1008 cells that are used in the Urbani SARS virucidal assay) that has been filtered through masks treated with Mosi-Guard™. This is a positive control for tCPE caused by Mosi-Guard™

Virus only control—cells incubated with virus that has not been filtered through the masks. This is a positive control for vCPE. It is also an indicator of the stock titre.

Mask only control—cells incubated with virus that has been filtered through masks not treated with Mosi-Guard™. This is a positive control for virus adsorption to the mask.

Antiviral control—cells incubated with virus that has not been filtered through the masks, but has been pre-treated with either citrate buffer at pH 3.5 (Influenza A/Sydney/5/97 virucidal assay) or 1% triton X-100/20% ethanol/PBS (Urbani SARS virucidal assay). This is a positive control for the test articles.

The viruses, and their appropriate cell lines, that were used in the study, are indicated in Table 9. They were supplied from the Retroscreen Virology Ltd virus repository and cell culture stocks.

TABLE 9

The viruses and their appropriate cell lines

| Virus | Stock tire (TCID$_{50}$/ml)$^\infty$ | Cell Line |
| --- | --- | --- |
| Influenza A/Sydney/5/97 | $10^3$ | Vero |
| Urbani SARS virus | $10^4$ | C1008 |

$^\infty$obtained from the virus control titres

Procedure

The procedure was divided into two phases:

Primary phase—testing against Influenza A/Sydney/5/97 to determine the incuation times and the appropriate number of sprays of Mosi-Guard™ to use in the testing against Urbani SARS virus.

Secondary phase—testing Urbani SARS virus using the specifics justified by the primary phase procedure.

Primary Phase

Preparation of Vero Cells

1) Cells (100 μl/well) at 1×10$^5$ cells/ml were seeded onto 96-well plates and incubated at 37° C. for ~24 hours.
2) The maintenance media on the plates was removed and the cell monolayer washed twice with PBS (100 μl/well).
3) PBS (200 μl/well) was added to the outer wells while infection media (100 μl/well) was added to the rest of the wells.

Addition and Incubation of Mosi-Guard™

4) Each mask was sprayed once with Mosi-Guard™ from a distance of ~15 cm.
5) Each mask was placed into individual paper autoclave bags and incubated at 37° C. for ~8 hours.

Filtration and Titration of Virus

6) The sprayed area, measuring a diameter of 2 cm, was cut out of each mask and inserted into filter holders (25 mm diameter Swin-Lok™ plastic filter holders).
7) Virus (2 ml) was filtered through each mask using the pressure exerted by a 150 g mass. This was carried out by placing a 150 g weight on the syringe.
8) The filtered virus (111 μl/well) and virus control were added, in quadruplicate, to the 96-well plate and titrated down the plate following a 10-fold dilution series. The virus control consisted of the stock virus that was added direct to the plate.
9) The plate was incubated at 37° C. for 4-5 days.
10) vCPE was scored on days 3-5 post-titration.

Haemagglutination Assay

11) On the final incubation day, an HA (haemagglutination) assay was performed on all plates as per Retroscreen Virology Ltd SOP VA018-02.

Secondary Phase

This was performed in an identical manner as the primary phase, with the exception of the following details:

C1008 cells were used and were seeded at 1.5×10$^5$ cells/ml (step 1).

The mask was sprayed 3× with Mosi-Guard™ (step 1).

Cells were not washed with PBS and, subsequently, infection media was not used (step 2 & 3). Urbani SARS virus infection can take place in the presence of standard cell maintenance media.

An HA assay was not performed as Urbani SARS virus does not possess the haemagglutinin protein that is specific to influenza viruses (step 11). Only vCPE observations were performed.

Results

Cytotoxicity Assay

Four different types of masks were sprayed once with Mosi-Guard™ and then incubated at 37° C. for ~8 hours. Cell media, appropriate to the cell line, was filtered through sections of each mask and the filtrate inoculated onto vero and C1008 cells and then titrated down the plate following a 10-fold dilution series. The cells were incubated for 1 (C1008 cells) and 3 days (vero cells) before they were observed and scored for tCPE. The results of these are indicated in Table 10 and 11, respectively.

TABLE 10

Cytotoxicity determination on C1008 cells after 1X spray of Mosi-guard ™ onto each mask

| Dilution Series | tCPE scores 1 day post-treatment at 37° C. Mask | | | |
| --- | --- | --- | --- | --- |
| (10$^{-x}$) | GR8-1 | GR8-2 | GR8-3 | GR8-4 |
| 0 | T | T | T | T |
| 1 | T | — | — | — |
| 2 | — | — | — | — |
| 3 | — | — | — | — |
| 4 | — | — | — | — |
| 5 | — | — | — | — |

T toxicity is observed
— no toxicity is observed

TABLE 11

Cytotoxicity determination on vero cells after 1X spray of Mosi-guard ™ onto each mask

| Dilution Series | tCPE scores 3 days post-treatment at 37° C. Mask | | | |
| --- | --- | --- | --- | --- |
| (10$^{-x}$) | GR8-1 | GR8-2 | GR8-3 | GR8-4 |
| 0 | T | — | — | — |
| 1 | — | — | — | — |
| 2 | — | — | — | — |
| 3 | — | — | — | — |
| 4 | — | — | — | — |
| 5 | — | — | — | — |

T toxicity is observed
— no toxicity is observed

Influenza A/Sydney/5/97 Virucidal Assay

The following tables show the log reduction in viral titre of Influenza A/Sydney/5/97 virus after it was filtered through for different types of masks that were either treated (Table 12) or not treated (Table 13) with one spray of Mosi-Guard™, and then incubated for ~8 hours at 37° C.

A reduction of $\geq 1-\log_{10}$ TCID$_{50}$/ml (Oxford, J. S. et al (1994) Antiv Chem Chemother 5(4): 176-81) is deemed significant for this assay and is equivalent to $\geq 90\%$ reduction in viral titre.

The threshold of sensitivity for the assay in this model was deemed to be 0.25–$\log_{10}$ TCID$_{50}$/ml.

TABLE 12 log reductions in viral titre of Influenza A/Sydney/5/97 virus after it was filtered though masks that were treated with Mosi-guard ™

| Mask | Viral titre ($\log_{10}$ TCID$_{50}$/ml) | | Log reduction in viral titre (-log10 TCID$_{50}$/ml) |
|---|---|---|---|
| | With Mosi-guard | Virus Control‡ | |
| GR8-1 | 1.25 | 2.50 | 1.25 |
| GR8-2 | 2.50 | 3.50 | 1.00 |
| GR8-3 | 2.50 | 3.50 | 1.00 |
| GR8-4 | 2.50 | 3.50 | 1.00 |

‡stock virus added directly to the plate

TABLE 13 log reductions in viral titre of Influenza A/Sydney/5/97 virus after it was filtered though masks that were not treated with Mosi-guard ™

| Mask | Viral titre ($\log_{10}$ TCID$_{50}$/ml) | | Log reduction in viral titre (-log10 TCID$_{50}$/ml) |
|---|---|---|---|
| | With Mosi-guard | Virus Control‡ | |
| GR8-1 | 2.50 | 2.50 | <0.25 |
| GR8-2 | 2.50 | 2.50 | <0.25 |
| GR8-3 | 2.50 | 2.50 | <0.25 |
| GR8-4 | 2.50 | 2.50 | <0.25 |

‡stock virus added directly to the plate

Urbani SARS Virucidal Assay

Table 14 and Table 15 show the log reductions in viral titre of Urbani SARS virus after it was filtered through one type of masks that was either treated or not treated with three sprays of Mosi-Guard™, respectively, and then incubated for ~8 hours at 37° C.

A reduction of ≧1–$\log_{10}$ TCID$_{50}$/ml (Oxford, J. S. et al (1994) Antiv Chem Chemother 5(4): 176-81) is deemed significant for this assay and is equivalent to ≧90% reduction in viral titre.

The threshold of sensitivity for the assay in this model was deemed to be 0.25–$\log_{10}$ TCID$_{50}$ ml.

TABLE 14 log reductions in viral titre of Urbani SARS virus after it was filtered through a mask that was treated with Mosi-guard ™

| Mask | Viral titre ($\log_{10}$ TCID$_{50}$/ml) | | Log reduction in viral titre (-log10 TCID$_{50}$/ml) |
|---|---|---|---|
| | With Mosi-guard | Virus Control‡ | |
| GR8-1 | 2.75 | 4.00 | 1.25 |

† actual value is in the negative, but within the variability of the assay system
‡stock virus added directly to the plate

TABLE 15 log reductions in viral titre of Urbani SARS virus after it was filtered through a mask that was not treated with Mosi-guard ™

| Mask | Viral titre ($\log_{10}$ TCID$_{50}$/ml) | | Log reduction in viral titre (-log10 TCID$_{50}$/ml) |
|---|---|---|---|
| | With Mosi-guard | Virus Control‡ | |
| GR8-1 | 3.75 | 3.75 | <0.25 |

† actual value is in the negative, but within the variability of the assay system
‡stock virus added directly to the plate Discussion Cytotoxicity Assay The results of the vero cytotoxicity assay (Table 11) suggest that the filtrate collected from mask GR8-1 exhibited toxicity as the undiluted concentration. The filtrate collected from masks GR8-2, GR8-3 and GR8-4, did not exhibit any toxicity against the vero cells.

The results of the C1008 cytotoxicity assay (Table 10) indicated that the filtrate collected from mask GR8-1, GR8-2, GR8-3 and GR8-4 exhibited toxicity at the undiluted concentration. The filtrate collected from mask GR8-1 also exhibited toxicity at the 10-fold dilution.

Influenza A/Sydney/5/97 Virucidal Assay

The results of the Influenza A/Syndy/5/97 virucidal assay (Table 12) indicated that one spray of Mosi-Guard™ on each mask was sufficient to reduce the viral titre by at least 1–$\log_{10}$ TCID$_{50}$. In addition to this, the results indicate that Mosi-Guard™ is still active, antivirally, against Influenza A/Sydney/5/97 after 8 hours at 37° C.

The results of the mask control are displayed in Table 13, which indicate that the process of filtering virus through the mask caused no detectable reduction in viral titre and, therefore, significant adsorption of the virus to the masks had not occurred.

Urbani SARS Virucidal Assay

The results of the Urbani SARS virucidal assay (Table 14) indicate that three sprays of Mosi-Guard™ on mask GR8-1 was sufficient to reduce the viral titre by 1.25–$\log_{10}$ TCID$_{50}$. In addition to this, the results indicate that Mosi-Guard™ is still active, antivirally, against Urbani SARS virus after 8 hours at 37° C.

The results of the mask control are displayed in Table 15. No detectable reductions in viral titre were exhibited by the filtrate collected from mask GR8-1. This indicates that the control mask did not absorb the virus significantly during the filtration process.

It will be appreciated that the invention may be modified within the scope of the appended claims.

The invention claimed is:

1. A method of destroying, inactivating, or inhibiting the growth or reproduction of a virus comprising administering an effective amount of p-menthane-3,8-diol (PMD) wherein the virus has a lipid envelope and wherein the virus is selected from the group consisting of influenza virus; A/Sydney/5/97 virus; virus causing Urbani Severe Acute Respiratory Syndrome (Urbani SARS); Herpes Simplex virus type-1 (HSV-1); and combinations thereof.

2. The method of claim 1 wherein the PMD is present in a composition optionally comprising a carrier.

3. The method of claim 2 wherein the amount of PMD in the composition is at least 0.25% w/v.

4. The method of claim 2 wherein the composition is a spray.

5. The method of claim 4 wherein the spray is formulated for nasal administration.

6. The method of claim 2 wherein the composition is a pharmaceutical composition or medicament.

7. The method of claim 6 wherein the pharmaceutical composition or medicament is used in vitro.

8. The method of claim 6 wherein the pharmaceutical composition or medicament is used in vivo.

9. The method of claim 1 wherein the administering is in non-therapeutic, non-surgical or non-diagnostic applications.

10. The method of claim 1 wherein the PMD is a crude or purified natural product or is a synthetic product.

11. The method of claim 1 wherein the PMD is provided in the form of PMD-rich extract derived from lemon eucalyptus.

12. The method of claim 1 wherein the administering further comprises applying the PMD to a surface to destroy, inactivate, or inhibit growth or reproduction of the virus on the surface.

13. The method of claim 1 wherein the administering further comprises applying the PMD to a face mask to destroy, inactivate, or inhibit growth or reproduction of the virus in contact with the face mask.

14. The method of claim 13 wherein the face mask comprises a replaceable filter, wherein the filter contains PMD.

15. The method of claim 1 wherein the administering further comprises adding or applying PMD to a sanitizing spray, sanitizing liquid, pre-wetted wipe, detergent, cleaner, cream, conditioner, hand gel, topical composition, toiletry, lotion, liniment, oil, ointment, cloth, article of clothing, molded article, countertop or work surface, building material or surface, equipment component or surface, or furniture component or surface.

* * * * *